United States Patent
Vidalain et al.

(10) Patent No.: US 9,315,482 B2
(45) Date of Patent: Apr. 19, 2016

(54) DERIVATIVES USEFUL AS ANTIVIRAL AGENTS

(75) Inventors: Pierre-Olivier Vidalain, Puteaux (FR); Marianne Lucas-Hourani, Paris (FR); Frédéric Tangy, Les Lilas (FR); Hélène Munier-Lehmann, Meudon (FR); Daniel Dauzonne, Paris (FR)

(73) Assignees: Institut Pasteur, Paris (FR); Centre National de la Recherche Scientifique, Paris (FR); Institut Curie, Paris (FR)

( * ) Notice: Subject to any disclaimer, the term of this patent is extended or adjusted under 35 U.S.C. 154(b) by 210 days.

(21) Appl. No.: 13/809,761

(22) PCT Filed: Jul. 29, 2011

(86) PCT No.: PCT/IB2011/053387
§ 371 (c)(1),
(2), (4) Date: Mar. 28, 2013

(87) PCT Pub. No.: WO2012/014181
PCT Pub. Date: Feb. 2, 2012

(65) Prior Publication Data
US 2013/0210886 A1    Aug. 15, 2013

(30) Foreign Application Priority Data

Jul. 29, 2010   (EP) .................................... 10290426

(51) Int. Cl.
| | | |
|---|---|---|
| C07D 307/79 | (2006.01) | |
| C07D 307/82 | (2006.01) | |
| C07D 307/86 | (2006.01) | |
| C07D 307/83 | (2006.01) | |
| C07D 405/04 | (2006.01) | |
| C07D 405/02 | (2006.01) | |
| C07D 493/04 | (2006.01) | |

(52) U.S. Cl.
CPC ............ *C07D 307/83* (2013.01); *C07D 307/82* (2013.01); *C07D 405/02* (2013.01); *C07D 405/04* (2013.01); *C07D 493/04* (2013.01)

(58) Field of Classification Search
CPC ............................. C07D 307/79; C07D 307/82
USPC .................................. 549/462, 469, 470, 471
See application file for complete search history.

(56) References Cited

FOREIGN PATENT DOCUMENTS

| CN | 101628904 A | * 1/2010 |
|---|---|---|
| EP | 0 853 083 | 7/1998 |

OTHER PUBLICATIONS

CN 101628904A Eglish translation, 2011.*
Chobanyan, Derivatives of Furan Based on Terminal Acetylenes, Russian Journal of Organic Chemistry, 5, p. 881, 1993.
Trukhin, Beta, Beta-Dinitrostyrenes in Reactions with Cyclohexane-1,3-Diones, Russian Chemical Bulletin, 58, pp. 2035-2038, 2009.

* cited by examiner

*Primary Examiner* — Shengjun Wang
(74) *Attorney, Agent, or Firm* — Morgan, Lewis & Bockius LLP

(57) ABSTRACT

The invention relates to compounds of formula (I) for use in the prevention and/or treatment of viral infections: Wherein X, Y, Z, T, $R^{1a}$ and $R^{1b}$ are as defined in claim 1.

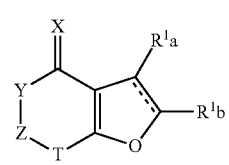

(I)

2 Claims, 11 Drawing Sheets

A

B

DERIVATIVES USEFUL AS ANTIVIRAL AGENTS

The present invention is related to compounds for use in the prevention and/or treatment of viral infections, pharmaceutical compositions, and processes for the preparation thereof.

Very few antiviral drugs active against RNA viruses are currently available. This is particularly worrisome since most of the highly pathogenic and emerging viruses are RNA viruses. These viruses can cause acute, severe illness, including severe respiratory disease, hemorrhagic fever and encephalitis, with a high case fatality rate. This problem is particularly acute for viruses of the Flavivirus genus, such as the West-Nile Virus, which has spread all over the United States during the last 10 years and was the cause for 32 deaths and 720 reported cases in that country in 2009.

Among the various therapeutic strategies for fighting RNA virus infections, small molecule inhibitors of viral infections appear particularly promising. However, small molecule inhibitor-based drugs currently approved for the treatment of RNA virus infections (other than HIV) are scarce. Notable examples include the influenza M2 channel inhibitors, amantadine and rimantadine; the influenza neuraminidase inhibitors, oseltamivir and zanamivir, and ribavirin for the treatment of infections with respiratory syncytial virus and hepatitis C virus.

Accordingly, most patients infected by RNA viruses, such as Flaviruses, cannot benefit from a treatment with such small molecule inhibitors, and it is a goal of current research to actively pursue the identification of new small molecule inhibitors potentially active against RNA virus infections.

In this regard, the identification of several such putative small molecule inhibitors has been recently reported, either by screening compound libraries and/or by targeting specific cellular mechanisms thought to be involved in virus replication. Thus, Goodell et al. (2006) *J. Med. Chem.* 49:2127-2137 and Puig-Basagoiti et al. (2006) *Antimicrob. Agents Chemother.* 50:1320-1329 disclose that pirazoline compounds identified by high-throughput screening could be useful for treating Flavivirus, in particular West Nile Virus, infections. In another instance, Dunn et al. (2009) 83:11665-11672 have identified that Akt inhibitor would be useful for treating RNA virus infections. However, none of these compounds has been validated for human use yet.

It is thus an object of the present invention to provide alternative compounds useful for treating infections by virus, in particular RNA virus.

The present invention in one aspect is directed to various compounds of structure:

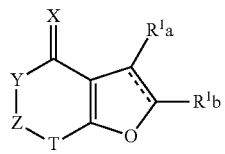

(I)

and its stereoisomeric forms, mixtures of stereoisomeric forms, or pharmaceutically acceptable salt forms thereof, wherein the constituent members are defined infra.

Another object of the present invention is to provide pharmaceutical compositions comprising the compounds of the present invention wherein the compositions comprise one or more pharmaceutically acceptable excipients and a therapeutically effective amount of at least one of the compounds of the present invention, or a pharmaceutically acceptable salt thereof.

Another object of the present invention is to provide compounds of formula (I) for use in the prevention and/or treatment of viral infections.

Another object of the present invention is to provide methods of treating or preventing viral infections comprising the administration of a therapeutically effective amount of a compound of formula (I) to a patient in need thereof.

These and other objects, features and advantages of the compounds of formula (I) will be disclosed in the following detailed description of the patent disclosure.

Compounds of Formula (I) for Use in the Prevention and/or Treatment of Viral Infections In a first object, the present invention provides compounds of formula (I) for use in the prevention and/or treatment of viral infections,

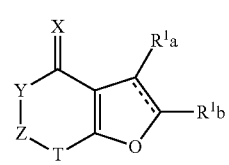

(I)

Wherein:

X is O, S, NOH, N—NH$_2$, or NR$^x$ wherein R$^x$ is H or C$_1$-C$_6$ alkyl;

Y is O, S, CH$_2$, or NR$^x$;

—Z-T- is —C(R$^2$)(R$^3$)—(CH$_2$)$_n$— or

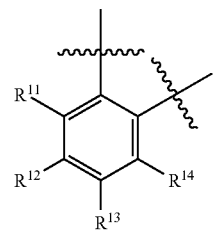

provided that when Y is CH$_2$, then Z-T- is —C(R$^2$)(R$^3$)—(CH$_2$)$_n$—, and provided that when Y is O, S, or NR$^x$, then Z-T- is

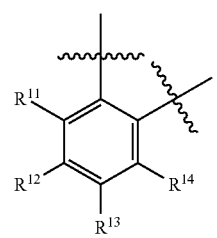

$R^2$, $R^3$ are H, $CH_3$, F, Cl, Br, I, $NR^iR^{ii}$, OH, C(=O)OH, $C_6$-$C_{10}$ aryl, or a 5 to 7 membered heterocycle;

$R^{1b}$ is H or $NO_2$;

$R^{1a}$ is a ring system A or B:

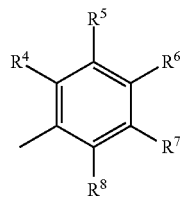

(A)

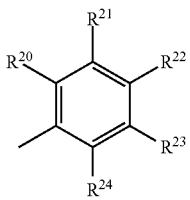

in which:

$R^{20}$, $R^{21}$, $R^{22}$, $R^{23}$, and $R^{24}$, are each independently selected from H, Cl, Br, I, F, OH, $C_1$-$C_6$ alkyl, $C_2$-$C_8$ alkenyl, $C_1$-$C_6$ fluoroalkyl, $C_1$-$C_6$ fluoroalkoxy, $NO_2$, and $C_1$-$C_6$ alkoxy, a heteroaryl selected from:

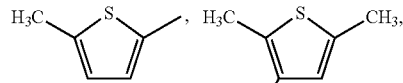

(B)

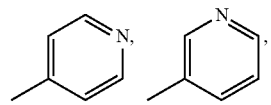

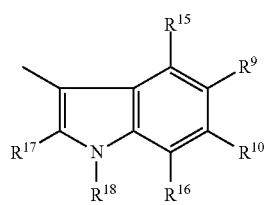

or two of $R^{20}$, $R^{21}$, $R^{22}$, $R^{23}$, $R^{24}$ together form with the carbon atoms to which they are attached a 1,3-dioxolane or 1,4-dioxane;

$R^4$, $R^5$, $R^6$, $R^7$ and $R^8$ are each independently selected from H, Cl, Br, I, F, OH, $C_1$-$C_6$ alkyl, $C_2$-$C_8$ alkenyl, $C_1$-$C_6$ fluoroalkyl, $C_1$-$C_6$ fluoroalkoxy, $NO_2$, and $C_1$-$C_6$ alkoxy, or two of $R^4$, $R^5$, $R^6$, $R^7$, $R^8$ together form with the carbon atoms to which they are attached a 1,3-dioxolane or 1,4-dioxane;

$R^9$, $R^{10}$ are each independently selected from H, $OCH_3$, F, Cl, Br, I, $NR^iR^{ii}$, OH, C(=O)$OR^{iii}$, $SO_3R^{iii}$, or $CH_2SO_3N(R^{iii})(R^{iv})$;

$R^{11}$ and $R^{14}$, are each independently selected from H, Cl, Br, I, F, $OR^v$, $CONHR^v$, $N(C_1$-$C_6$ alkyl$)_2$, $C_1$-$C_6$ alkyl, $C_1$-$C_6$ fluoroalkyl, $C_1$-$C_6$ fluoroalkoxy, $NO_2$, and $C_1$-$C_6$ alkoxy, or $R^{11}$ and $R^{14}$ together form a 1,3-dioxolane or 1,4-dioxane;

$R^{12}$ and $R^{13}$, are each independently selected from H, Cl, Br, I, F, $OR^v$, $CONHR^v$, $N(C_1$-$C_6$ alkyl$)_2$, $C_1$-$C_6$ alkyl, $C_1$-$C_6$ fluoroalkyl, $C_1$-$C_6$ fluoroalkoxy, $NO_2$, $C_1$-$C_6$ alkoxy, $-(CH_2)_{n''}COOR^{iii}$, $-(CH_2)CON(R^{iii})_2$, or a

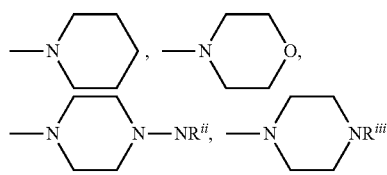

cycle, or $R^{12}$ and $R^{13}$ together form a 1,3-dioxolane or 1,4-dioxane;

$R^{15}$ is H;

$R^{16}$ is H or a $C_1$-$C_6$ linear or branched alkyl;

$R^{17}$ is selected from H, a $C_1$-$C_6$ linear, branched or cyclic alkyl, SH, $(CH_2)_{n'}$—$COOR^v$, F, Cl, Br, I, or an aryl of formula:

$R^{18}$ is selected among:

—H,

—$SO_2R'$, $COR'$, or $(CH_2)_nNR'_2$ wherein R' is a linear or branched $C_1$-$C_6$ alkyl, $C_6$-$C_{10}$ aryl, or a benzyl group, —$(CH_2)_{n'}COOR''$, $(CH_2)_{n'}CONR''_2$, or $(CH_2)_{n'}OR''$, wherein R'' is H, a linear or branched $C_1$-$C_6$ alkyl, $C_6$-$C_{10}$ aryl, or a benzyl group, —$CH_2R'''$, or $COCH_2R'''$, wherein R''' is H, a linear or branched $C_1$-$C_6$ alkyl, or $C_6$-$C_{10}$ aryl, —$SiR''''_3$, wherein R'''' is H, or a linear or branched $C_1$-$C_6$ alkyl;

$R^i$ and $R^{ii}$ are, at each occurrence, independently selected from H, $C_1$-$C_6$ alkyl, or together form with the nitrogen atom to which they are attached a 5 to 7 membered heterocycle;

and $R^{iii}$ and $R^{iv}$ are, at each occurrence, independently selected from H, or $C_1$-$C_6$ alkyl;

$R^v$ is, at each occurrence, independently selected from H, or $C_1$-$C_6$ alkyl, or $C_6$-$C_{10}$ aryl;

n is 1 or 2;

n' is selected from 0 to 6, and preferably is 1 or 2;

n'' is selected from 0 to 8, and preferably from 2 to 6;

R is $C_1$-$C_6$ alkyl;

---- is either a single or double bond;

and the stereoisomeric forms, mixtures of stereoisomeric forms or pharmaceutically acceptable salts forms thereof.

According to preferred embodiment, the invention concerns the following compounds of formula (I) for use in the prevention and/or treatment of viral infections:

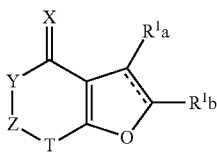

Wherein:
X is O, S, NOH, N—NH$_2$, or NR;
Y is O or CH$_2$;
—Z-T- is —C(R$^2$)(R$^3$)—(CH$_2$)$_n$— or

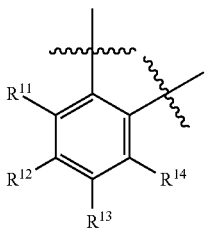

provided that when Y is CH$_2$, then Z-T- is —C(R$^2$)(R$^3$)—(CH$_2$)$_n$—, and
provided that when Y is O, then Z-T- is

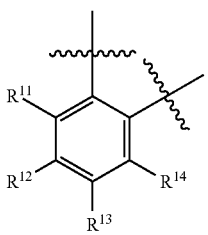

R$^2$, R$^3$ are H and/or CH$_3$;
R$^{1b}$ is H or NO$_2$;
R$^{1a}$ is a ring system A or B:

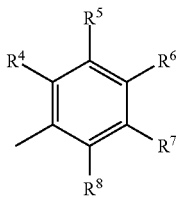

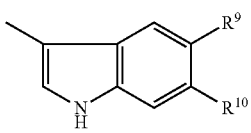

R$^4$, R$^5$, R$^6$, R$^7$ and R$^8$ are each independently selected from H, Cl, Br, I, F, OH, C$_1$-C$_6$ alkyl, C$_1$-C$_6$ fluoroalkyl, C$_1$-C$_6$ fluoroalkoxy, NO$_2$, and C$_1$-C$_6$ alkoxy, or two of R$^4$, R$^5$, R$^6$, R$^7$, R$^8$ together form with the carbon atoms to which they are attached a 1,3-dioxolane or a 1,4-dioxane cycle;
R$^9$, R$^{10}$ are each independently selected from H and OCH$_3$;
R$^{11}$, R$^{12}$, R$^{13}$, and R$^{14}$ are each independently selected from H, Cl, Br, I, F, OH, C$_1$-C$_6$ alkyl, C$_1$-C$_6$ fluoroalkyl, C$_1$-C$_6$ fluoroalkoxy, NO$_2$, and C$_1$-C$_6$ alkoxy, or two of R$^{11}$, R$^{12}$, R$^{13}$, R$^{14}$ together form with the carbon atoms to which they are attached a 1,3-dioxolane or 1,4-dioxane;
n is 1 or 2;
R is C$_1$-C$_6$ alkyl;
---- is either a single or double bond;
and the stereoisomeric forms, mixtures of stereoisomeric forms or pharmaceutically acceptable salts forms thereof.

Preferably, X is O.
In a preferred aspect, ---- is a double bond.
In certain aspects, there are included compounds of formula (I) wherein —Z-T- is —C(R$^2$)(R$^3$)—(CH$_2$)$_n$—.
Preferably, n is 1.
Preferably, R$^2$ and R$^3$ are H.
In other aspects of the present invention, there are included compounds of formula (I) wherein R$^4$ and R$^8$ are H.
In additional aspects of the present invention, there are included compounds of formula (I) wherein at least one of R$^5$, R$^6$, R$^7$ is selected from I, Cl, Br, or —CH═CH$_2$, the others being H.
In certain aspects, there are included compounds of formula (I) wherein R$^{1a}$ and R$^{1b}$ are in a trans configuration.
Preferably, the compound of formula (I) for use in the prevention or treatment of viral infections is selected from:
3-(5-chloro-2-methoxyphenyl)-6,7-dihydro-5,1-benzofuran-4-one
3-(3-bromophenyl)-6,7-dihydro-5H-benzofuran-4-one
3-(3-fluorophenyl)-6,7-dihydro-5H-benzofuran-4-one
3-(4-chlorophenyl)-6,7-dihydro-5H-benzofuran-4-one
3-(2-chlorophenyl)-6,7-dihydro-5H-benzofuran-4-one
3-(3-methoxyphenyl)-6,7-dihydrobenzofuran-4(5H)-one
3-(3,5-dichlorophenyl)-6,7-dihydro-5H-benzofuran-4-one
3-(3-nitrophenyl)-6,7-dihydro-5H-benzofuran-4-one
3-((3-trifluoromethyl)phenyl)-6,7-dihydro-5H-benzofuran-4-one
3-(3-benzyloxyphenyl)-6,7-dihydro-5H-benzofuran-4-one
3-(3,4,5-trimethoxyphenyl)-6,7-dihydro-5H-benzofuran-4-one
3-(3,4-dichlorophenyl)-6,7-dihydro-5H-benzofuran-4-one
3-(3-iodo-4-methoxyphenyl)-6,7-dihydro-5H-benzofuran-4-one
3-(3-iodophenyl)-6,7-dihydro-5H-benzofuran-4-one
3-(3-chlorophenyl)-6,7-dihydro-5H-benzofuran-4-one
3-(3-chlorophenyl)-6,6-dimethyl-6,7-dihydro-5H-benzofuran-4-one
3-(3-chlorophenyl)-6-methyl-6,7-dihydro-5H-benzofuran-4-one
3-(5-chloro-2-methoxyphenyl)-2-nitro-3,5,6,7-tetrahydro-2H-benzofuran-4-one
3-(2-chlorophenyl)-2-nitro-3,5,6,7-tetrahydro-2H-benzofuran-4-one
1-[4-(3-chlorophenyl)-2-methyl-5-nitro-4,5-dihydrofuran-3-]ethanone
3-(1H-Indol-3-yl)-2-nitro-2,3-dihydrofuro[3,2-c]chromen-4-one
3-(3-Chlorophenyl)-6,7-dihydro-5H-benzofuran-4-one oxime
3-(3-iodophenyl)-6,7-dihydro-5H-benzofuran-4-one (GAC 25)
3-(3-ethenylphenyl)-6,7-dihydro-5H-benzofuran-4-one (GAC 50)
3-(3-methylphenyl)-6,7-dihydro-5H-benzofuran-4-one (GAC 22)
3-(2,3-dichlorophenyl)-6,7-dihydro-5H-benzofuran-4-one (GAC 20)
3-(1H-Indol-3-yl)-8-chloro-2-nitro-2,3-dihydrofuro[3,2-c]chromen-4-one (DD771)

3-(1H-Indol-3-yl)-8-fluoro-2-nitro-2,3-dihydrofuro[3,2-c]chromen-4-one (DD776)

3-(1H-Indol-3-yl)-8-methyl-2-nitro-2,3-dihydrofuro[3,2-c]chromen-4-one (DD778).

Pharmaceutical Compositions

In another object, the present invention relates to a pharmaceutical composition comprising a compound of formula (I) as above, in admixture with one or more pharmaceutically acceptable excipients.

In certain aspects of the invention, there is included pharmaceutical compositions comprising a compound of formula (I) as defined hereabove wherein:

when Y is O and Z-T- is

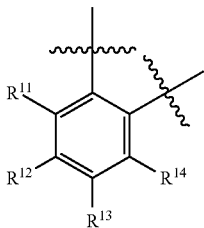

then $R^{1a}$ cannot be a ring system A.

Compounds of Formula (I)

In another object, the present invention relates to a compound of formula (I):

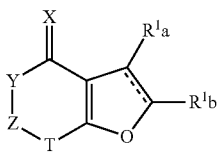

Wherein

X, Y, Z, T, $R^{1a}$, and $R^{1b}$ are as defined above, with the proviso that:

when $R^2$ and $R^3$ are $CH_3$, then $R^{1b}$ cannot be $NO_2$; and when Z-T- is

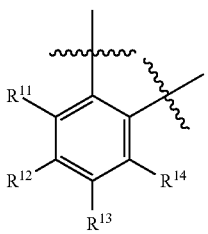

then $R^{1a}$ cannot be a ring system A;

and with the exclusion of the compounds of formula (I) wherein:

X is O; $R^{1b}$ is $NO_2$; $R^2$=$R^3$ is H; $R^{1a}$ is Ph, m- or p-$NO_2$Ph, or p-ClPh; n is 1; and ---- is a single bond;

X is O; $R^{1b}$ is H or $NO_2$; $R^2$=$R^3$ are H or $CH_3$; $R^{1a}$ is m- or p-$NO_2$Ph; n is 1; and ---- is a double bond;

X is O; $R^{1b}$ is H; $R^2$=$R^3$ are H; $R^{1a}$ is Ph; n is 1; and ---- is a single bond;

and the stereoisomeric forms, mixtures of stereoisomeric forms or pharmaceutically acceptable salts forms thereof.

In an aspect of the invention, there is provided compounds of formula (I), wherein ---- is a single bond, with the proviso that:

when $R^2$ and $R^3$ are $CH_3$, then $R^{1b}$ cannot be $NO_2$;

and with the exclusion of the compounds of formula (I) wherein:

X is O; $R^{1b}$ is $NO_2$; $R^2$=$R^3$ is H; $R^{1a}$ is Ph, m- or p-$NO_2$Ph, or p-ClPh; n is 1; and ---- is a single bond;

X is O; $R^{1b}$ is H; $R^2$=$R^3$ are H; $R^{1a}$ is Ph; n is 1; and ---- is a single bond;

and the stereoisomeric forms, mixtures of stereoisomeric forms or pharmaceutically acceptable salts forms thereof.

In a preferred aspect of the invention, the compound of formula (I) has the following formula (Ia):

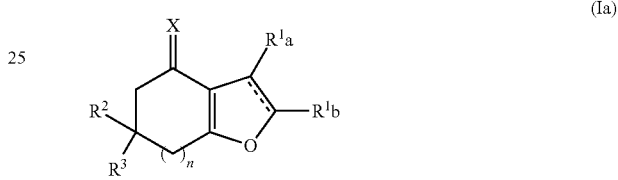

Wherein X, $R^{1a}$, $R^{1b}$, $R^2$, $R^3$ and n are as defined above, with the proviso that:

when $R^2$ and $R^3$ are $CH_3$, then $R^{1b}$ cannot be $NO_2$;

and with the exclusion of the compounds of formula (I) wherein:

X is O; $R^{1b}$ is $NO_2$; $R^2$=$R^3$ is H; $R^{1a}$ is Ph, m- or p-$NO_2$Ph, or p-ClPh; n is 1; and ---- is a single bond;

X is O; $R^{1b}$ is H or $NO_2$; $R^2$=$R^3$ are H or $CH_3$; $R^{1a}$ is m- or p-$NO_2$Ph; n is 1; and ---- is a double bond;

X is O; $R^{1b}$ is H; $R^2$=$R^3$ are H; $R^{1a}$ is Ph; n is 1; and ---- is a single bond;

and the stereoisomeric forms, mixtures of stereoisomeric forms or pharmaceutically acceptable salts forms thereof.

In a preferred aspect, in the above formula (Ia), $R^{1a}$ is a ring system A having the following formula ($Ia_1$):

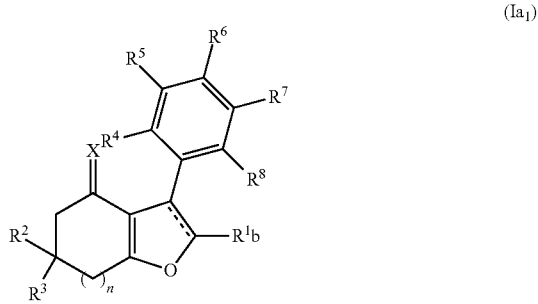

wherein n, $R^{1b}$, $R^2$, $R^3$, $R^4$, $R^5$, $R^6$, $R^7$ and $R^8$ are as defined above.

In another preferred aspect of the invention, the compound of formula (I) has the following formula (Ib'):

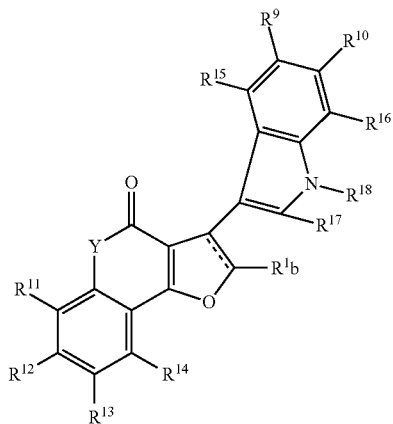

wherein Y is selected among O, S, or $NR^x$, and $R^x$, $R^{1b}$, $R^9$, $R^{10}$, $R^{11}$, $R^{12}$, $R^{13}$, $R^{14}$, $R^{15}$, $R^{16}$, $R^{17}$ and $R^{18}$ are as defined above.

According to a preferred embodiment, the compound of formula (I) has the following formula (Ib):

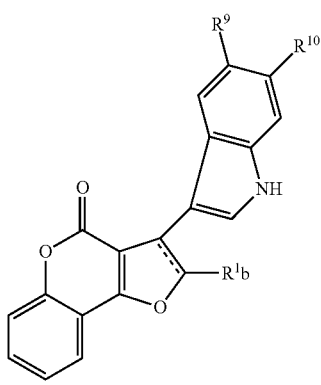

wherein $R^{1b}$, $R^9$ and $R^{10}$ are as defined above.

Preferably, the compound of formula (I) is selected from:
3-(5-chloro-2-methoxyphenyl)-6,7-dihydro-5H-benzofuran-4-one
3-(3-bromophenyl)-6,7-dihydro-5H-benzofuran-4-one
3-(3-fluorophenyl)-6,7-dihydro-5H-benzofuran-4-one
3-(4-chlorophenyl)-6,7-dihydro-5H-benzofuran-4-one
3-(2-chlorophenyl)-6,7-dihydro-5H-benzofuran-4-one
3-(3-methoxyphenyl)-6,7-dihydrobenzofuran-4(5H)-one
3-(3,5-dichlorophenyl)-6,7-dihydro-5H-benzofuran-4-one
3-((3-trifluoromethyl)phenyl)-6,7-dihydro-5H-benzofuran-4-one
3-(3-benzyloxyphenyl)-6,7-dihydro-5H-benzofuran-4-one
3-(3,4,5-trimethoxyphenyl)-6,7-dihydro-5H-benzofuran-4-one
3-(3,4-dichlorophenyl)-6,7-dihydro-5H-benzofuran-4-one
3-(3-iodo-4-methoxyphenyl)-6,7-dihydro-5H-benzofuran-4-one
3-(3-iodophenyl)-6,7-dihydro-5H-benzofuran-4-one
3-(3-chlorophenyl)-6,7-dihydro-5H-benzofuran-4-one
3-(3-chlorophenyl)-6,6-dimethyl-6,7-dihydro-5H-benzofuran-4-one
3-(3-chlorophenyl)-6-methyl-6,7-dihydro-5H-benzofuran-4-one
3-(5-chloro-2-methoxyphenyl)-2-nitro-3,5,6,7-tetrahydro-2H-benzofuran-4-one
3-(2-chlorophenyl)-2-nitro-3,5,6,7-tetrahydro-2H-benzofuran-4-one
1-[4-(3-chlorophenyl)-2-methyl-5-nitro-4,5-dihydrofuran-3-yl]ethanone
3-(1H-Indol-3-yl)-2-nitro-2,3-dihydrofuro[3,2-c]chromen-4-one
3-(3-Chlorophenyl)-6,7-dihydro-5H-benzofuran-4-one oxime
3-(3-iodophenyl)-6,7-dihydro-5H-benzofuran-4-one (GAC 25)
3-(3-ethenylphenyl)-6,7-dihydro-5H-benzofuran-4-one (GAC 50)
3-(3-methylphenyl)-6,7-dihydro-5H-benzofuran-4-one (GAC 22)
3-(2,3-dichlorophenyl)-6,7-dihydro-5H-benzofuran-4-one (GAC 20)
3-(1H-Indol-3-yl)-8-chloro-2-nitro-2,3-dihydrofuro[3,2-c]chromen-4-one (DD771)
3-(1H-Indol-3-yl)-8-fluoro-2-nitro-2,3-dihydrofuro[3,2-c]chromen-4-one (DD776)
3-(1H-Indol-3-yl)-8-methyl-2-nitro-2,3-dihydrofuro[3,2-c]chromen-4-one (DD778).

Most preferably, the compound of formula (I) is selected from:
3-(3-chlorophenyl)-6,7-dihydro-5H-benzofuran-4-one, and
3-(1H-Indol-3-yl)-2-nitro-2,3-dihydrofuro[3,2-c]chromen-4-one
3-(3-iodophenyl)-6,7-dihydro-5H-benzofuran-4-one (GAC 25)
3-(3-ethenylphenyl)-6,7-dihydro-5H-benzofuran-4-one (GAC 50)
3-(1H-Indol-3-yl)-8-chloro-2-nitro-2,3-dihydrofuro[3,2-c]chromen-4-one (DD771)
3-(1H-Indol-3-yl)-8-fluoro-2-nitro-2,3-dihydrofuro[3,2-c]chromen-4-one (DD776)
3-(1H-Indol-3-yl)-8-methyl-2-nitro-2,3-dihydrofuro[3,2-c]chromen-4-one (DD778).

DEFINITIONS

The following terms and expressions contained herein are defined as follows:

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_6$ alkyl" refers to an alkyl radical containing from 1 to 6 carbon atoms.

As used herein, the term "alkenyl" refers to a straight chain, or branched hydrocarbon chains of 2 to 8 carbon atoms having at least one carbon-carbon double bond. A designation "$C_2$-$C_8$ alkenyl" refers to an alkenyl radical containing from 2 to 8 carbon atoms. Examples of alkenyl groups include ethenyl, propenyl, isopropenyl, 2,4-pentadienyl, etc.

As used herein, the term "alkoxy" means an alkyl-O— group wherein the alkyl group is as herein described. Exemplary alkoxy groups include methoxy, ethoxy, n-propoxy, i-propoxy, n-butoxy and heptoxy.

As used herein, the term "fluoroalkyl" means an alkyl group substituted by one or more fluorine atoms. "Fluoroalkyl" groups are notably perfluoroalkyl groups of formula $C_nF_{2n+1}$, such as trifluoromethyl ($CF_3$).

As used herein, the term "fluoroalkoxy" means an alkoxy group substituted by one or more fluorine atoms. "Fluoroalkoxy" groups are notably perfluoroalkoxy groups of formula $C_nF_{2n+1}O$—, such as trifluoromethoxy ($CF_3O$).

As used herein, the terms "heterocycle", "heterocyclic" or "heterocyclyl" refer to a mono- di-, tri- or other multicyclic aliphatic ring system that includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups.

As used herein, the term "heterocycloalkyl" refers to a cycloalkyl group in which one or more ring carbon atoms are replaced by at least one hetero atom such as —O—, —N—, or —S—, and includes ring systems which contain a saturated ring group bridged or fused to one or more aromatic groups. Some heterocycloalkyl groups containing both saturated and aromatic rings include phthalamide, phthalic anhydride, indoline, isoindoline, tetrahydroisoquinoline, chroman, isochroman, and chromene.

As used herein, the term "aryl" refers to a simple or substituted aromatic ring containing 5 to 10 ring carbon atoms.

As used herein, the term "heteroaryl" refers to an aryl group containing 5 to 10 ring carbon atoms in which one or more ring carbon atoms are replaced by at least one hetero atom such as —O—, —N—, or —S—. Some heteroaryl groups of the present invention include pyridyl, pyrimidyl, pyrrolyl, furanyl, thienyl, imidazolyl, triazolyl, tetrazolyl, quinolyl, isoquinolyl, benzoimidazolyl, thiazolyl, pyrazolyl, and benzothiazolyl groups.

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The meanings of all the other terms used in the description of the present invention are well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker: New York, 1992, incorporated by reference herein in its entirety.

It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods for resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

Synthesis

The compounds of the present invention may be prepared in a number of methods well known to those skilled in the art, including, but not limited to those described below, or through modifications of these methods by applying standard techniques known to those skilled in the art of organic synthesis. They notably can be prepared according to the method disclosed in Daniel Dauzonne et al., Tetrahedron 1990, 46, 7359-7371. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

As will be readily understood, functional groups present on the compounds of Formula I may contain protecting groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Other preferred protecting groups according to the invention may be found in Greene, T. W. and Wuts, P. G. M., "Protective Groups in Organic Synthesis" 2d. Ed., Wiley & Sons, 1991.

The general route to prepare the examples of the present invention are shown in scheme 1 below. The reagents and starting materials are commercially available, or readily synthesized by well-known techniques by one of ordinary skill in the arts. All substituents in the synthetic Scheme 1, unless otherwise indicated, are as previously defined.

Thus, in a further object, the invention provides a method of preparation of a compound of formula (I), said method comprising:
i) reacting a compound of formula (II) with a compound of formula (III) wherein Hal is an halogen atom; and optionally
ii) recovering the obtained compound of formula (I).

Scheme 1

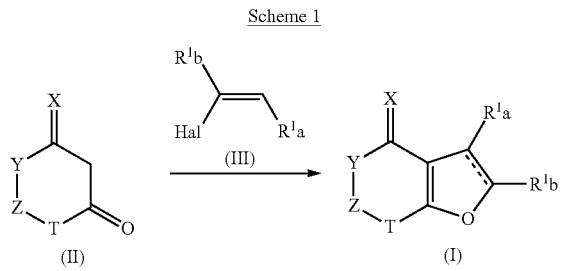

Generally step i) is performed in the presence of a fluoride salt, such as KF, in a solvent such as 1,2-dimethoxyethane under reflux.

Step i) may also be performed at room temperature in the presence of 1,8-diazabicyclo[5.4.0]undec-7-ene (DBU), in a solvent such as tetrahydrofuran.

Other features of the invention will become apparent in the course of the following descriptions of exemplary embodiments. These examples are given for illustration of the invention and are not intended to be limiting thereof.

EXAMPLES

Synthesis

Examples 1 to 17

Preparation of Compounds of Formula (I)

Figure 1:
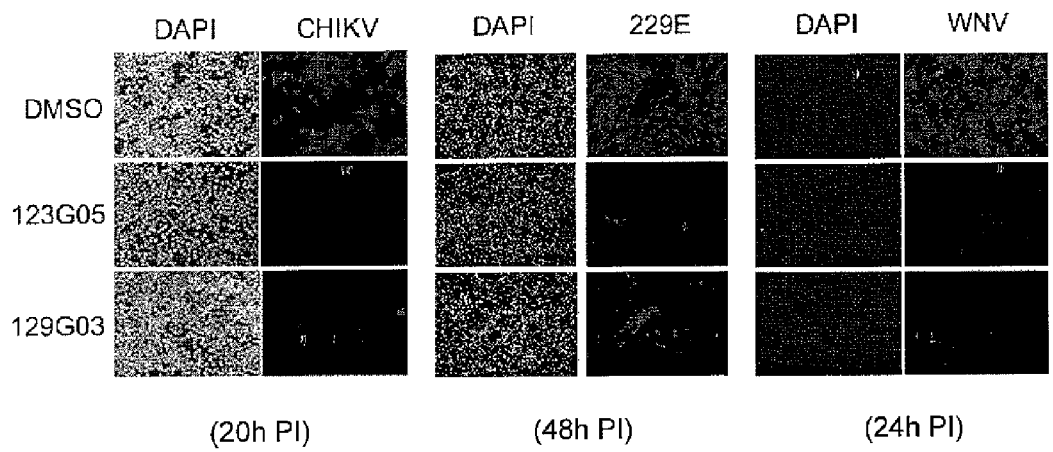
FIG. 1: Inhibition of chikungunya virus (CHIKV), human coronavirus 229E (229E), and West-Nile virus (WNV).

Analysis:

Melting points were measured on a Köfler hot stage apparatus and are uncorrected. Infrared spectra were recorded on a Perkin-Elmer RX I spectrophotometer as deuteriochloroform solutions or KBr discs. The $^1$H-NMR (300 MHz) were recorded on a Varian AC 300 spectrometer. Chemical shifts are expressed as parts per million downfield from tetramethylsilane. Splitting patterns have been designated as follows: s (singlet), d (doublet), dd (doublet of doublet), ddd (doublet of doublet of doublet), t (triplet), dt (doublet of triplet), q (quadruplet), quint (quintuplet) m (multiplet), br. (broad signal). Coupling constants (J values) are listed in hertz (Hz). Mass spectra were obtained with a ZQ 2000 MS spectrometer applying an electrospray (ES)$^+$ ionization technique.

The 3-aryl-6,7-dihydro-5H-benzofuran-4-ones DD697, DD700, DD701, DD703, DD706, DD710, DD711, DD718, GAC11, GAC13, GAC14, GAC15, GAC18, GAC25 and ICC005-L129-003 (see examples 1 to 15) were prepared on a 5 mmol scale from cyclohexane-1, 3-dione and the appropriate (Z)-β-chloro-β-nitrostyrenes according to a procedure previously published (Daniel DAUZONNE, Hubert JOSIEN and Pierre DEMERSEMAN *Tetrahedron* 1990, 46, 7359-7371). The syntheses of the 6-substituted derivatives DD694 (example 16) and DD720 (example 17) were performed starting from (Z)-1-Chloro-3-(2-chloro-2-nitroethenyl) benzene and dimedone or racemic 5-methylcyclohexane-1,3-dione, respectively.

Example 1

3-(5-chloro-2-methoxyphenyl)-6,7-dihydro-5H-benzofuran-4-one DD697

Yield 65%; mp 136-137° C. recrystallized from a benzene/heptane mixture.
IR (CDCl$_3$) $v_{max}$ (cm$^{-1}$): 1672
$^1$H NMR (CDCl$_3$) δ (ppm): 2.20 (quint, 2H, J=6.4 Hz), 2.51 (br t, 2H, J=6.4 Hz), 2.92 (t, 2H, J=6.4 Hz), 3.78 (s, 3H), 6.85 (d, 1H, J=8.8 Hz), 7.25 (dd, 1H, J=2.6 Hz and 8.8 Hz), 7.43 (d, 1H, J=2.6 Hz), 7.47 (s, 1H).
MS (m/z): 277-279 [M+H]$^+$, 299-301 [M+Na]$^+$.

Example 2

3-(3-bromophenyl)-6,7-dihydro-5H-benzofuran-4-one DD700

Yield 71%; mp 106-107° C. recrystallized from heptane.
IR (CDCl$_3$) $v_{max}$ (cm$^{-1}$): 1678, 1220
$^1$H NMR (CDCl$_3$) δ (ppm): 2.20 (quint, 2H, J=6.5 Hz), 2.55 (br t, 2H, J=6.5 Hz), 2.93 (t, 2H, J=6.5 Hz), 7.24 (t, 1H, J=7.9 Hz), 7.43 (s, 1H), 7.44 (ddd, 1H, J=1.1 Hz, 1.8 Hz and 7.9 Hz), 7.58 (dt, 1H, J=1.1 Hz and 7.9 Hz), 7.76 (t, 1H, J=1.8 Hz).
MS (m/z): 291-293 [M+H]$^+$, 313-315 [M+Na]$^+$.

Example 3

3-(3-fluorophenyl)-6,7-dihydro-5H-benzofuran-4-one DD701

Yield 78%; mp 65-66° C. recrystallized from heptane.
IR (CDCl$_3$) $v_{max}$ (cm$^{-1}$): 1678, 1217
$^1$H NMR (CDCl$_3$) δ (ppm): 2.21 (quint, 2H, J=6.4 Hz), 2.56 (br t, 2H, J=6.4 Hz), 2.94 (t, 2H, J=6.4 Hz), 6.96-7.04 (m, 1H), 7.26-7.42 (m, 3H), 7.45 (s, 1H).
MS (m/z): 231 [M+H]$^+$, 253 [M+Na]$^+$.

Example 4

3-(4-chlorophenyl)-6,7-dihydro-5H-benzofuran-4-one DD703

Yield 81%; mp 104-105° C. (with allotropic change at 100-102° C.) recrystallized from heptane.
IR (CDCl$_3$) $v_{max}$ (cm$^{-1}$): 1674, 1216
$^1$H NMR (CDCl$_3$) δ (ppm): 2.20 (quint, 2H, J=6.4 Hz), 2.54 (br t, 2H, J=6.4 Hz), 2.93 (t, 2H, J=6.4 Hz), 7.30-7.36 (A part of AA'BB' system, 2H, J$_{app}$=8.7 Hz), 7.42 (s, 1H), 7.53-7.58 (B part of AA'BB' system, 2H, J$_{app}$=8.7 Hz).
MS (m/z): 247-249 [M+H]$^+$, 269-271 [M+Na]$^+$.

Example 5

3-(2-chlorophenyl)-6,7-dihydro-5H-benzofuran-4-one DD706

Yield 77%; mp 147-148° C. recrystallized from heptane.
IR (CDCl$_3$) $v_{max}$ (cm$^{-1}$): 1672, 1006
$^1$H NMR (CDCl$_3$) δ (ppm): 2.21 (quint, 2H, J=6.4 Hz), 2.50 (br t, 2H, J=6.4 Hz), 2.95 (t, 2H, J=6.4 Hz), 7.21-7.31 (m, 2H), 7.32-7.39 (m, 1H), 7.40 (s, 1H).
MS (m/z): 247-249 [M+H]$^+$, 269-271 [M+Na]$^+$.

Example 6

3-(3-methoxyphenyl)-6,7-dihydrobenzofuran-4(5H)-one DD710

Yield 85%; mp 79-80° C. recrystallized from heptane.
IR (CDCl$_3$) $v_{max}$ (cm$^{-1}$): 1674, 1221
$^1$H NMR (CDCl$_3$) δ (ppm): 2.20 (quint, 2H, J=6.4 Hz), 2.55 (br t, 2H, J=6.4 Hz), 2.93 (t, 2H, J=6.4 Hz), 3.85 (s, 3H), 6.87 (ddd, 1H, J=1.0 Hz, 2.6 Hz and 8.2 Hz), 7.17 (dt, 1H, J=1.2 Hz and 7.7 Hz), 7.24-7.31 (m, 2H), 7.45 (s, 1H).
MS (m/z): 243 [M+H]$^+$, 265 [M+Na]$^+$.

Example 7

3-(3,5-dichlorophenyl)-6,7-dihydro-5H-benzofuran-4-one DD711

Yield 87%; mp 105-106° C. (with allotropic change at 98-100° C.) recrystallized from heptane.
IR (CDCl$_3$) $v_{max}$ (cm$^{-1}$): 1676, 1216
$^1$H NMR (CDCl$_3$) δ (ppm): 2.21 (quint, 2H, J=6.4 Hz), 2.56 (br t, 2H, J=6.4 Hz), 2.93 (t, 2H, J=6.4 Hz), 7.29 (t, 1H, J=1.9 Hz), 7.46 (s, 1H), 7.54 (d, 2H J=1.9 Hz).
MS (m/z): 303-305-307 [M+Na]$^+$.

Example 8

3-(3-nitrophenyl)-6,7-dihydro-5H-benzofuran-4-one DD718

Yield 63%; mp 94-95° C. recrystallized from a benzene/heptane mixture.
IR (CDCl$_3$) $v_{max}$ (cm$^{-1}$): 1678, 1529, 1350, 1216
$^1$H NMR (CDCl$_3$) δ (ppm): 2.23 (quint, 2H, J=6.3 Hz), 2.57 (br t, 2H, J=6.3 Hz), 2.96 (t, 2H, J=6.3 Hz), 7.54 (t, 1H, J=8.0 Hz), 7.55 (s, 1H), 8.01 (dt, 1H, J=1.1 Hz and 8.0 Hz), 8.16 (ddd, 1H, J=1.1 Hz, 2.0 Hz and 8.0 Hz), 8.48 (t, 1H, J=2.0 Hz).
MS (m/z): 258 [M+H]$^+$, 280 [M+Na]$^+$.

Example 9

3-((3-trifluoromethyl)phenyl)-6,7-dihydro-5H-benzofuran-4-one GAC11

Yield 85%; mp 134-135° C. recrystallized from heptane.
IR (CDCl$_3$) $v_{max}$ (cm$^{-1}$): 1776, 1726, 1678, 1216
$^1$H NMR (CDCl$_3$) δ (ppm): 2.21 (quint, 2H, J=6.4 Hz), 2.57 (br t, 2H, J=6.4 Hz), 2.95 (t, 2H, J=6.4 Hz), 7.49 (s, 1H), 7.45-7.60 (m, 2H), 7.84 (d, 1H, J=7.7 Hz), 7.88 (br s, 1H).
MS (m/z): 303 [M+Na]$^+$.

Example 10

3-(3-benzyloxyphenyl)-6,7-dihydro-5H-benzofuran-4-one GAC13

Yield 74%; yellow oil.
IR (CDCl$_3$) $\nu_{max}$ (cm$^{-1}$): 1674, 1234
$^1$H NMR (CDCl$_3$) δ (ppm): 2.20 (quint, 2H, J=6.4 Hz), 2.56 (br t, 2H, J=6.4 Hz), 2.93 (t, 2H, J=6.4 Hz), 5.12 (s, 2H), 6.95 (ddd, 1H, J=1.3 Hz, 2.6 Hz and 8.2 Hz), 7.21 (dt, 1H, J=1.3 Hz and 7.8 Hz), 7.24-7.50 (m, 8H).
MS (m/z): 341 [M+Na]$^+$.

Example 11

3-(3,4,5-trimethoxyphenyl)-6,7-dihydro-5H-benzofuran-4-one GAC14

Yield 83%; mp 140-141° C. recrystallized from a benzene/heptane mixture.
IR (CDCl$_3$) $\nu_{max}$ (cm$^{-1}$): 1663, 1505, 1130
$^1$H NMR (CDCl$_3$) δ (ppm): 2.21 (quint, 2H, J=6.3 Hz), 2.56 (br t, 2H, J=6.3 Hz), 2.94 (t, 2H, J=6.3 Hz), 3.87 (s, 3H), 3.90 (s, 6H), 7.26 (s, 2H), 7.46 (s, 1H).
MS (m/z): 325 [M+Na]$^+$.

Example 12

3-(3,4-dichlorophenyl)-6,7-dihydro-5H-benzofuran-4-one GAC15

Yield 91%; mp 122-123° C. recrystallized from heptane.
IR (CDCl$_3$) $\nu_{max}$ (cm$^{-1}$): 1674, 1216
$^1$H NMR (CDCl$_3$) δ (ppm): 2.21 (quint, 2H, J=6.3 Hz), 2.55 (br t, 2H, J=6.3 Hz), 2.94 (t, 2H, J=6.3 Hz), 7.43 (d, 1H, J=8.4 Hz), 7.45 (s, 1H), 7.50 (dd, 1H J=2.1 Hz and 8.4 Hz), 7.73 (d, 1H, J=2.1 Hz).
MS (m/z): 303-305-307 [M+Na]$^+$.

Example 13

3-(3-iodo-4-methoxyphenyl)-6,7-dihydro-5,1-benzofuran-4-one GAC18

Yield 76%; mp 197-198° C. recrystallized from a benzene/heptane mixture.
R (CDCl$_3$) $\nu_{max}$ (cm$^{-1}$): 1673, 1488, 1215
$^1$H NMR (CDCl$_3$) δ (ppm): 2.20 (quint, 2H, J=6.4 Hz), 2.54 (br t, 2H, J=6.4 Hz), 2.92 (t, 2H, J=6.4 Hz), 3.89 (s, 3H), 6.84 (d, 1H, J=8.4 Hz), 7.37 (s, 1H), 7.65 (dd, 1H, J=2.1 Hz and 8.4 Hz), 8.00 (d, 1H, J=2.1 Hz).
MS (m/z): 391 [M+Na]$^+$.

Example 14

3-(3-iodophenyl)-6,7-dihydro-5H-benzofuran-4-one GAC25

Yield 79%; mp 135-136° C. recrystallized from heptane.
IR (CDCl$_3$) $\nu_{max}$ (cm$^{-1}$): 1675, 1220
$^1$H NMR (CDCl$_3$) δ (ppm): 2.20 (quint, 2H, J=6.4 Hz), 2.55 (br t, 2H, J=6.4 Hz), 2.93 (t, 2H, J=6.4 Hz), 7.11 (t, 1H, J=7.8 Hz), 7.43 (s, 1H), 7.59-7.67 (m, 2H), 7.96 (t, 1H, J=1.7 Hz).
MS (m/z): 361 [M+Na]$^+$.

Example 15

3-(3-chlorophenyl)-6,7-dihydro-5H-benzofuran-4-one ICC005-L129-G03

Yield 72%; mp 87-88° C. recrystallized from heptane.
IR (CDCl$_3$) $\nu_{max}$ (cm$^{-1}$): 1675, 1216
$^1$H NMR (CDCl$_3$) δ (ppm): 2.21 (quint, 2H, J=6.3 Hz), 2.55 (br t, 2H, J=6.3 Hz), 2.94 (t, 2H, J=6.3 Hz), 7.26-7.34 (m, 2H), 7.44 (s, 1H), 7.50-7.56 (m, 1H), 7.61 (dd, 1H, J=1.0 Hz and 2.1 Hz)
MS (m/z): 247-249 [M+H]$^+$, 269-271 [M++Na]$^+$.

Example 16

3-(3-chlorophenyl)-6,6-dimethyl-6,7-dihydro-5H-benzofuran-4-one DD694

Yield 77%; mp 104-105° C. recrystallized from heptane.
IR (CDCl$_3$) $\nu_{max}$ (cm$^{-1}$): 1677, 1215
$^1$H NMR (CDCl$_3$) δ (ppm): 1.17 (s, 6H), 2.44 (s, 2H), 2.80 (s, 2H), 7.27-7.34 (m, 2H), 7.47 (s, 1H), 7.53-7.58 (m, 1H), 7.64 (dd, 1H, J=0.5 Hz and 1.8 Hz).
MS (m/z): 275-277 [M+H]$^+$, 297-299 [M+Na]$^+$.

Example 17

3-(3-chlorophenyl)-6-methyl-6,7-dihydro-5H-benzofuran-4-one DD720

Yield 81%; mp 121-122° C. (with allotropic change at 116-118° C.) recrystallized from heptane.
IR (CDCl$_3$) $\nu_{max}$ (cm$^{-1}$): 1676
$^1$H NMR (CDCl$_3$) δ (ppm): 1.20 (d, 3H, J=6.0 Hz), 2.31 (dd, 1H, J=10.4 Hz and 15.5 Hz), 2.39-2.66 (m, 3H), 3.02 (dd, 1H, J=4.5 Hz and 15.9 Hz), 7.24-7.34 (m, 2H), 7.45 (s, 1H), 7.49-7.57 (m, 1H), 7.62 (brs, 1H).
MS (m/z): 261-263 [M+H]$^+$, 283-285 [M+Na]$^+$.

Examples 18 to 21

The trans 3-aryl-2-nitro-3,5,6,7-tetrahydro-2H-benzofuran-4-ones DD698 (example 18) and DD707 (example 19) were synthesized on a 5 mmol scale from cyclohexane-1,3-dione and the appropriate (Z)-β-chloro-β-nitrostyrenes according to a modified methodology formerly described (Daniel DAUZONNE and Pierre DEMERSEMAN *J. Heterocyclic Chem.* 1990, 27, 1581-1584). Compounds GAC5 (example 20) and ICC005-L123-G05 (example 21) were obtained by applying the same procedure to the relevant reagents, i. e. (Z)-1-Chloro-3-(2-chloro-2-nitroethenyl)benzene and acetylacetone in the first case or (Z)-3-(2-Chloro-2-nitroethenyl)-1H-indole and 2,4-dihydroxycoumarine in the second case.

Example 18

3-(5-chloro-2-methoxyphenyl)-2-nitro-3,5,6,7-tetrahydro-2H-benzofuran-4-one DD 698

Yield 76%; mp 171-172° C. recrystallized from a benzene/heptane mixture.
IR (CDCl$_3$) $\nu_{max}$ (cm$^{-1}$): 1654, 1571, 1394, 1216
$^1$H NMR (CDCl$_3$) δ (ppm): 2.17-2.31 (m, 2H), 2.38-2.58 (m, 2H), 2.71-2.81 (m, 2H), 3.86 (s, 3H), 4.89 (br s, 1H), 5.88

(d, 1H, J=2.5 Hz), 6.83 (d, 1H, J=2.4 Hz), 6.84 (d, 1H, J=8.7 Hz), 7.25 (dd, 1H, J=2.4 Hz and 8.7 Hz).
MS (m/z): 346-348 [M+Na]$^+$.

Example 19

3-(2-chlorophenyl)-2-nitro-3,5,6,7-tetrahydro-2H-benzofuran-4-one DD 707

Yield 87%; mp 162-163° C. recrystallized from a benzene/heptane mixture.

IR (CDCl$_3$) $\nu_{max}$ (cm$^{-1}$): 1660, 1573, 1392, 1215
$^1$H NMR (CDCl$_3$) δ (ppm): 2.17-2.33 (m, 2H), 2.43-2.50 (m, 2H), 2.70-2.85 (m, 2H), 5.08 (br d, 1H, J=2.3 Hz), 5.95 (d, 1H, J=2.3 Hz), 6.98 (dd, 1H, J=2.2 Hz and 7.2 Hz), 7.19-7.31 (m, 2H), 7.45 (dd, 1H, J=1.9 Hz and 7.4 Hz).
MS (m/z): 316-318 [M+Na]$^+$.

Example 20

1-[4-(3-chlorophenyl)-2-methyl-5-nitro-4,5-dihydro-furan-3-yl]ethanone GAC 5

Yield 79%; mp 84-85° C. recrystallized from a benzene/heptane mixture.

IR (CDCl$_3$) $\nu_{max}$ (cm$^{-1}$): 1642, 1620, 1573, 1366, 1215
$^1$H NMR (CDCl$_3$) δ (ppm): 2.10 (s, 3H), 2.56 (s, 3H), 4.64 (br d, 1H, J=1.8 Hz), 5.08 (br d, 1H, J=1.8 Hz), 5.71 (d, 1H, J=1.8 Hz), 7.11-7.17 (m, 1H), 7.18-7.22 (m, 1H), 7.31-7.36 (m, 2H).
MS (m/z): 282-284 [M+H]$^+$, 304-306 [M+Na]$^+$.

Example 21

3-(1H-Indol-3-yl)-2-nitro-2,3-dihydrofuro[3,2-c]chromen-4-one ICC005-L123-G05

Yield 81%; mp 248-250° C. (dec.) recrystallized from toluene.

IR (Kbr disc) $\nu_{max}$ (cm$^{-1}$): 1716, 1658, 1564, 1498, 1408, 1371
$^1$H NMR (DMSO-d$_6$) δ (ppm): 5.38 (brd, 1H, 1.9 Hz), 6.96 (d, 1H, J=1.9 Hz), 7.06 (t, 1H, J=7.4 Hz), 7.14 (t, 1H, J=7.4 Hz), 7.33 (d, 1H, J=2.4 Hz), 7.40 (d, 1H, J=8.1 Hz), 7.52 (t, 1H, J=7.4 Hz), 7.58 (d, 1H, J=8.2 Hz), 7.60 (d, 1H, J=7.4 Hz), 7.81 (dt, 1H, J=1.5 Hz and 7.7 Hz), 7.92 (dd, 1H, J=1.5 Hz and 7.7 Hz), 11.42 (br s, 1H),
MS (m/z): 349 [M+H]$^+$, 371 [M+Na]$^+$.

Example 22

3-(3-Chlorophenyl)-6,7-dihydro-5H-benzofuran-4-one oxime GAC12

Following a classical procedure, the oxime GAC12 was prepared on a 2.5 mmol scale from the ketone ICC005-L129-G03 by refluxing overnight in ethanol, in the presence of a slight excess of pyridine, a mixture of this compound with hydroxylamine hydrochloride.

Yield 92%; mp 157-158° C. recrystallized from heptane.
IR (CDCl$_3$) $\nu_{max}$ (cm$^{-1}$): 3306, 3019, 1602, 1566, 1425, 1216

$^1$H NMR (CDCl$_3$) δ (ppm): 2.00 (quint, 2H, J=6.5 Hz), 2.68-2.82 (m, 4H), 7.23-7.28 (m, 2H), 7.29 (s, 1H), 7.33-7.40 (m, 1H), 7.50 (br s, 1H).
MS (m/z): 262-264 [M+H]$^+$, 284-286 [M+Na]$^+$.

Example 23

3-(3-ethenylphenyl)-6,7-dihydro-5H-benzofuran-4-one GAC50

Yield 79%; mp 88-89° C. recrystallized from heptane.

IR (CDCl$_3$) $\nu_{max}$ (cm$^{-1}$): 1675, 1412, 1005, 915
$^1$H NMR (CDCl$_3$) δ (ppm): 2.21 (quint, 2H, J=6.4 Hz), 2.56 (br t, 2H, J=6.4 Hz), 2.94 (t, 2H, J=6.4 Hz), 5.26 (brd, 1H, J=10.9 Hz), 5.79 (dd, 1H, J=0.6 Hz and 17.6 Hz), 6.74 (dd, 1H, J=10.9 Hz and 17.6 Hz), 7.30-7.40 (m, 2H), 7.45 (s, 1H), 7.51 (dt, 1H, J=1.8 Hz and 6.8 Hz)), 7.68 (brs, 1H).
MS (m/z): 261 [M+Na]$^+$.

Example 24

3-(1H-5-chloroindol-3-yl)-2-nitro-2,3-dihydrofuro[3,2-c]chromen-4-one DD771

Yield 78%; 263-265° C. dec. recrystallized from toluene/acetonitrile.

$^1$H NMR (DMSO-d$_6$) δ (ppm): 5.41 (d, 1H, 1.8 Hz), 6.98 (d, 1H, J=1.8 Hz), 7.07 (dt, 1H, J=1.0 Hz and 7.4 Hz), 7.14 (dt, 1H, J=1.0 Hz and 7.5 Hz), 7.35 (d, 1H, J=2.4 Hz), 7.40 (d, 1H, J=8.0 Hz), 7.61 (d, 1H, J=7.6 Hz), 7.63 (d, 1H, J=8.9 Hz), 7.85 (dd, 1H, J=2.5 Hz and 8.9 Hz), 7.95 (d, 1H, J=2.5 Hz), 11.23 s, 1H).
MS (m/z): 383, 385 [M+H]$^+$, 405, 407 [M+Na]$^+$.

Example 25

3-(1H-5-fluoroindol-3-yl)-2-nitro-2,3-dihydrofuro[3,2-c]chromen-4-one DD776

Yield 79%; mp 238-239° C. dec. recrystallized from toluene/acetonitrile.

$^1$H NMR (DMSO-d$_6$) δ (ppm): 5.41 (d, 1H, 1.8 Hz), 6.99 (d, 1H, J=1.8 Hz), 7.07 (t, 1H, J=7.4 Hz), 7.15 (t, 1H, J=7.2 Hz), 7.35 (d, 1H, J=2.4 Hz), 7.46 (d, 1H, J=7.9 Hz), 7.61 (d, 1H, J=7.8 Hz), 7.63-7.80 (m, 314), 11.23 (br s, 1H).
MS (m/z): 367 [M+H]$^+$, 389 [M+Na]$^+$.

Example 26

3-(1H-5-methylindol-3-yl)-2-nitro-2,3-dihydrofuro[3,2-c]chromen-4-one DD778

Yield 81%; mp 255-258° C. dec. recrystallized from toluene/acetonitrile.

$^1$H NMR (DMSO-d$_6$) δ (ppm): 2.47 (s, 3H), 5.49 (d, 1H, 1.8 Hz), 6.98 (d, 1H, J=1.8 Hz), 7.07 (t, 1H, J=7.4 Hz), 7.16 (t, 1H, J=7.5 Hz), 7.34 (d, 1H, J=2.3 Hz), 7.42 (d, 1H, J=8.0 Hz), 7.49 (d, 1H, J=8.5 Hz), 7.61 (d, 1H, J=8.3 Hz), 7.63 (d, 1H, J=.9.0 Hz), 7.74 (s, 1H), 11.24 (br s, 1H).
MS (m/z): 363 [M+H]$^+$, 385 [M+Na]$^+$.

Biological Data

Example 27

Inhibition of Chikungunya Virus (CHIKV), Human Coronavirus 229E (229E), and West-Nile Virus (WNV)

HEK293T cells or MRC5 cells were plated at $2.10^{+5}$ cells/well in a 24-wells plate and cultured overnight in 1 ml of DMEM (Dulbecco's Modified Eagle Medium) supplemented with 10% FCS (Fetal Calf Serum). Culture medium was supplemented with DMSO, 123-G05, or 129-G03, and cells were infected with CHIKV (Multiplicity Of Infection, M.O.I.=0.1), 229E (M.O.I.=0.01) or WNV (M.O.I.=1). CHIKV and WNV infections were performed on HEK-293T cells, whereas 229E infection was performed on MRC5 cells. Compounds were used at 2.5, 20, and 5 µg/ml to block CHIKV, 229E and WNV infection, respectively. Virus glycoprotein expression was determined by immunostaining at indicated times post-infection (PI) using specific antibodies (red fluorescence). CHIKV glycoprotein E2 was immunostained with Cy3-conjugated monoclonal antibody 3E4 (Bréhin & al., Virology, 2008, 371(1):185-95). 229E spike glycoprotein was immunostained with monoclonal antibody 5-11H.6 (Bonavia et al., Journal of Virology, 1997, 71(1): 800-6). WNV glycoprotein was immunostained with Cy3-conjugated monoclonal antibody E4. Cells were counterstained with DAPI (Blue fluorescence).

The results are set out in FIG. 1 and demonstrate that both 129-G03 and 123-G05 blocked the in vitro replication of all tested RNA viruses.

Example 28

Inhibition of Dengue Virus Replication in HEK-293T Cells

HEK-293T cells were plated at $2.10^{+5}$ cells/well in a 24-wells plate and cultured overnight in 1 ml of DMEM supplemented with 10% FCS. Cell cultures were supplemented with DMSO alone (0.2%), 123-G05 (5 µg/ml; 10 µg/ml; 20 µg/ml), or 129-G03 (5 µg/ml; 10 µg/ml; 20 µg/ml) in 10% FCS medium, and dengue virus (serotype 4) was immediately added in order to infect cells at 0.1 M.O.I. Cell cultures were incubated for an extra 72 h, and harvested. Culture medium was removed, and cells were fixed in 90% acetone. Finally, infected cells were stained for dengue virus glycoprotein expression using a 1/1000 dilution of a specific antibody (clone 1H10-6; Millipore) in PBS+5% goat serum. Immunostaining was revealed with a secondary Cy3-conjugated anti-mouse antibody.

Figure 2:
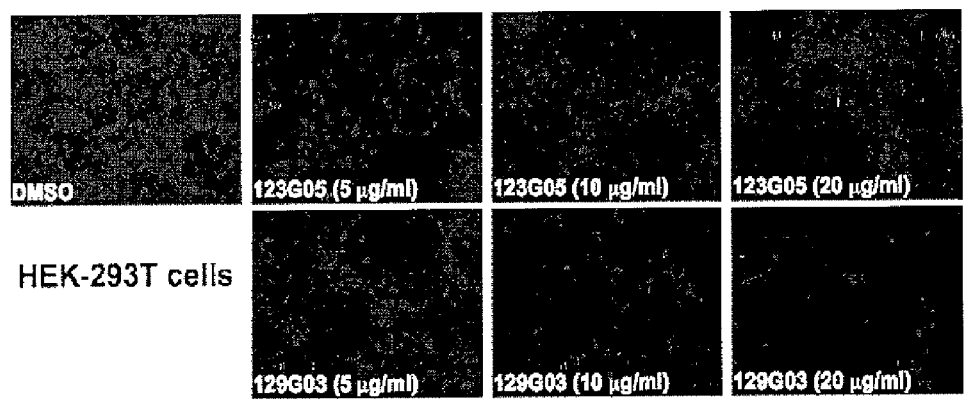
FIG. 2: Inhibition of dengue virus replication in HEK-293T cells.

The results set out in FIG. 2 show that both 129-G03 and 123-G05 blocked the in vitro replication of dengue virus (serotype 4).

Example 29

Inhibition of Human Parainfluenza Virus Type 3 in HEK-293T Cells

HEK-293T cells were plated at $2.10^{+5}$ cells/well in a 24-wells plate and cultured overnight in 1 ml of DMEM supplemented with 10% FCS. Cell cultures were supplemented with DMSO alone (0.2%), 123-G05 (2.5 µg/ml; 5 µg/ml; 10 µg/ml; 20 µg/ml), or 129-G03 (2.5 µg/ml; 5 µg/ml; 10 µg/ml; 20 µg/ml) in 10% FCS medium. Human parainfluenza virus type 3 (hPIV3) was immediately added in order to infect cells at 1 M.O.I. Cell cultures were incubated for an extra 48 h, and harvested. Culture medium was removed, and cells were fixed in 90% acetone. Infected cells were stained with a FITC-conjugated monoclonal antibody (17-038; Argene) to detect the virus glycoprotein (green fluorescence). Cells were counterstained with Evans blue (red fluorescence).

Figure 3:
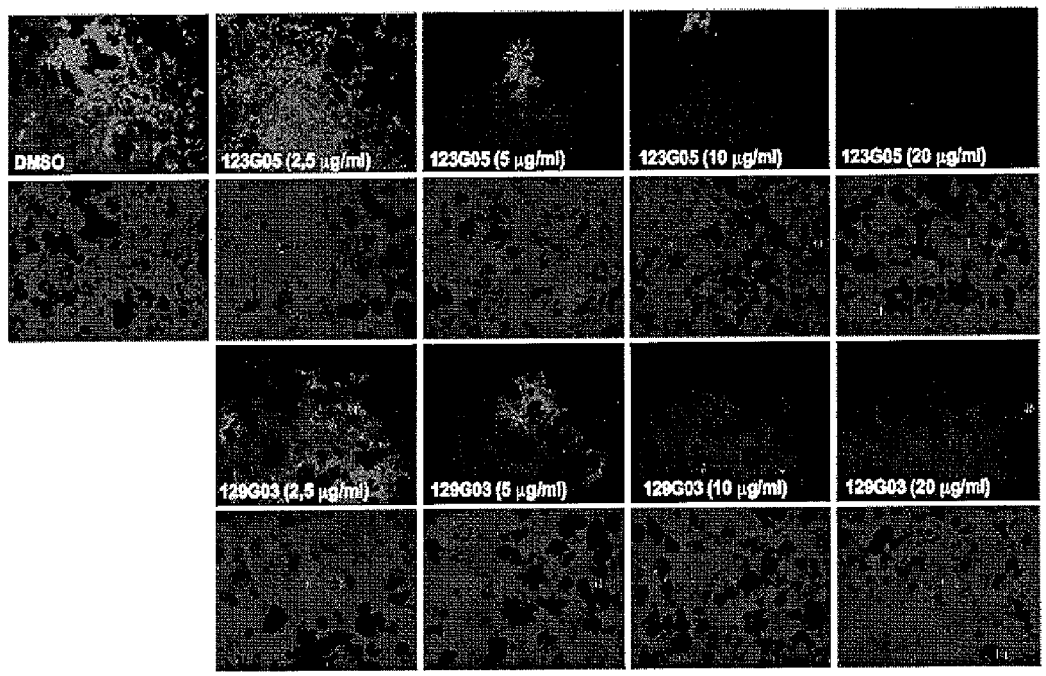
FIG. 3: Inhibition of human parainfluenza virus type 3 in HEK-293T cells.

The results set out in FIG. 3 show that both 129-G03 and 123-G05 blocked the in vitro replication of human parainfluenza virus type 3.

Example 30

Inhibition of Human Respiratory Syncytial Virus (RSV) in MRC5 Cells

MRC5 cells were plated at $10^{+5}$ cells/well in a 24-wells plate, and cultured in 1 ml of DMEM+10% FCS supplemented with DMSO alone (0.2%), 123-G05 (20 µg/ml; 10 µg/ml), 129-G03 (20 µg/ml; 10 µg/ml), or recombinant IFN-β ($10^{+3}$ IU/ml). After 24 h, cell culture medium was removed, and cells were incubated for at 37° C. in the presence RSV A2 or RSV B1 at a M.O.I of 1. After 1 h, viral supernatant was removed and replaced with fresh DMEM+10% FCS supplemented with DMSO, 123-G05 or 129-G03 using concentrations indicated above. After 48 h, cells were harvested, treated with Cytofix/Cytoperm fixation/permeabilization solution (Becton-Dickinson), and stained with anti-H antibodies (ab20391, Abeam) to detect the virus glycoprotein. The percentage of infected cells was determined by flow cytometry analysis. Interferon beta (IFN-β) was used as a reference.

Figure 4:
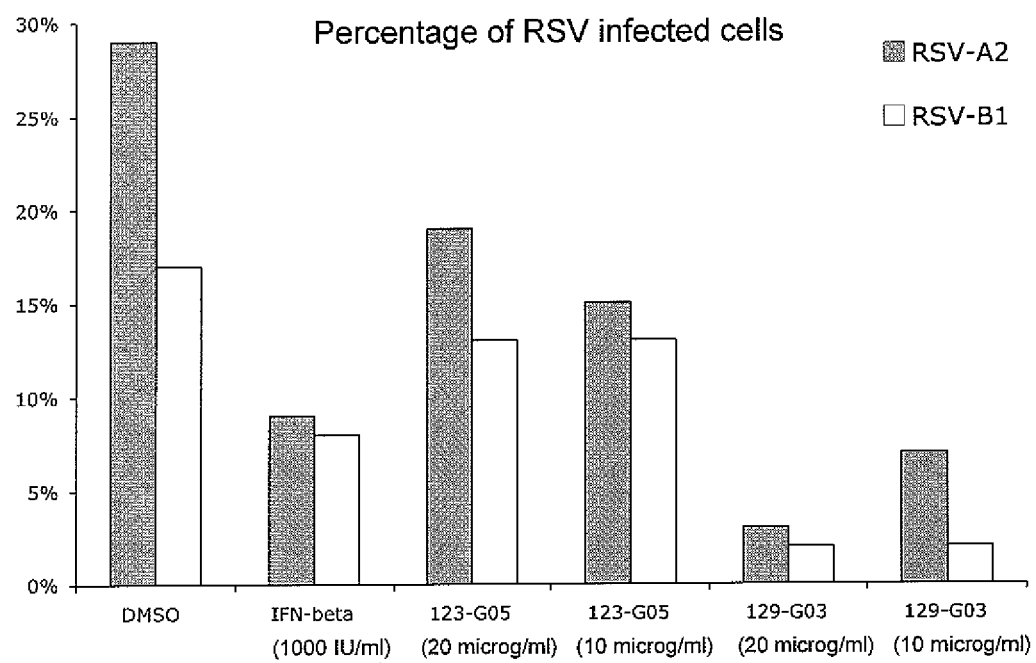
FIG. 4: Inhibition of human respiratory syncytial virus in MRC5 cells.

The results set out in FIG. 4 show that both 129-G03 and 123-G05 blocked the in vitro replication of hRSV (serotype A2 or B1).

Example 31

Inhibition of Coxsackievirus B3 in HEK-293T Cells

HEK-293T cells were plated at $2.10^{+5}$ cells/well in a 24-wells plate and cultured overnight in 1 ml of DMEM supplemented with 10% FCS. Cell cultures were supplemented with DMSO alone (0.1%), 123-G05 (10 µg/ml), 129-G03 (10 µg/ml), or recombinant IFN-β ($10^{+3}$ IU/ml) in 10% FCS medium, and coxsackievirus B3 was immediately added in order to infect cells at 0.1 M.O.I. Cultures were incubated for an extra 24 h. Finally, supernatants were harvested, and virus titers were determined by TCID50 (Tissue Culture Infecting Dose) on vera cells.

Figure 5:
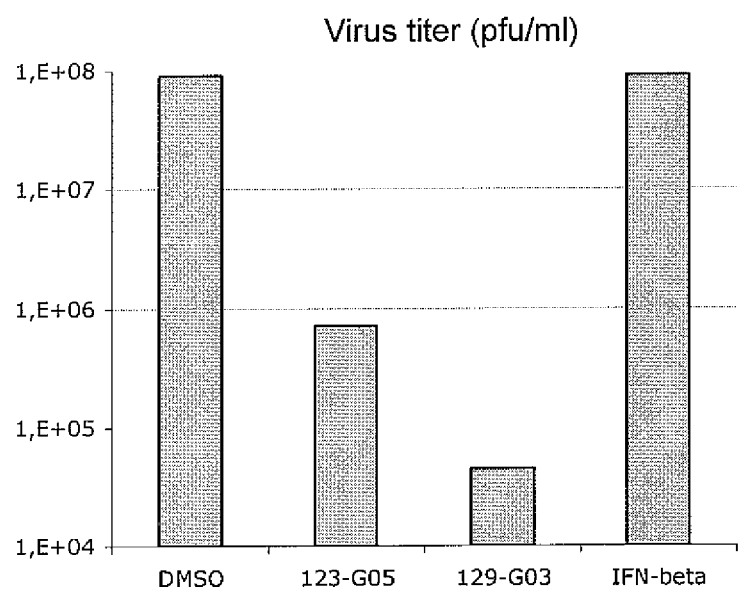
FIG. 5: Inhibition of coxsackievirus B3 in HEK-293T cells.

The results set out in FIG. 5 show that both 129-G03 and 123-G05 blocked the in vitro production of coxsackievirus B3.

Example 32

Inhibition of Measles Virus Replication in HEK-293T Cells

HEK-293T cells were plated at $2.10^{+5}$ cells/well in a 24-wells plate and cultured overnight in 1 ml of DMEM supplemented with 10% FCS. Cell cultures were supplemented with DMSO alone (0.2%; 0.1%; 0.05%), or 129-G03 (20 µg/ml; 10 µg/ml; 5 µg/ml) in 10% FCS medium. Measles virus with an additional transcription unit expressing luciferase was immediately added in order to infect cells at 1 M.O.I. Cultures were incubated for an extra 48 h. Cells were finally harvested and luciferase activity was determined in total cell lysates following manufacturer's recommendations (Dual-Glo Luciferase assay system; Promega).

Figure 6:
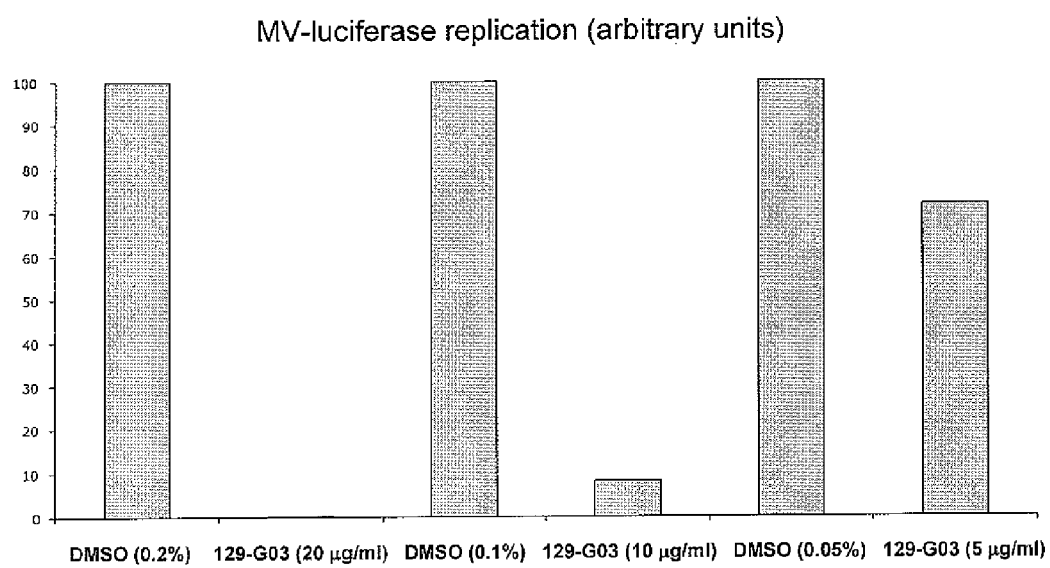
FIG. 6: Inhibition of measles virus replication in HEK-293T cells, by 129-G03.

The results set out in FIG. 6 show that both 129-G03 and 123-G05 blocked the in vitro replication of measles virus.

As a conclusion, ICC005-L-129-G03 and ICC005-L-123-G05 (referred later as 129-G03 and 123-G05, respectively), were selected for their ability to stimulate the ISRE-luciferase construct and the absence of cytotoxic effects on HEK-293T cells. These two molecules were subsequently tested for their antiviral activity against nine RNA viruses including measles virus, human respiratory syncytial virus (genotypes A2 and B1), human parainfluenza virus type 3, West-Nile virus, dengue virus, chikungunya virus, coxsackievirus B3, and human Coronavirus 229E. Two DNA viruses were also tested, including herpes simplex virus 1 (HSV1) and 2 (HSV2). Both 129-G03 and 123-G05 blocked the in vitro replication of all tested RNA viruses as assessed by immunostaining of infected cell cultures (FIGS. 1, 2, and 3), flow cytometry analysis (FIG. 4), virus titers measured in the supernatant of infected cells (FIG. 5) or using a recombinant virus expressing luciferase (FIG. 6).

In contrast, no effects were observed against HSV1 and HSV2. These two molecules blocked RNA virus replication at concentrations ranging from 2.5 to 20 µg/ml depending on the virus considered, with no detectable cytopathic effects. This inhibitory activity was observed in HEK-293T, MRC5, HuH-7, Jeg3, HeLa and A549 cell lines as well as human peripheral blood lymphocytes. This demonstrates that the antiviral activity of 129-G03 and 123-G05 is not cell-type specific.

Example 33

Inhibition of Measles Virus Replication in HEK-293T Cells

Cells were infected with a recombinant measles virus expressing luciferase, and treated with DMSO alone, or 129-G03, or GAC25 at indicated doses. After 48 h, luciferase activity was determined in total cell lysates.

Figure 7:
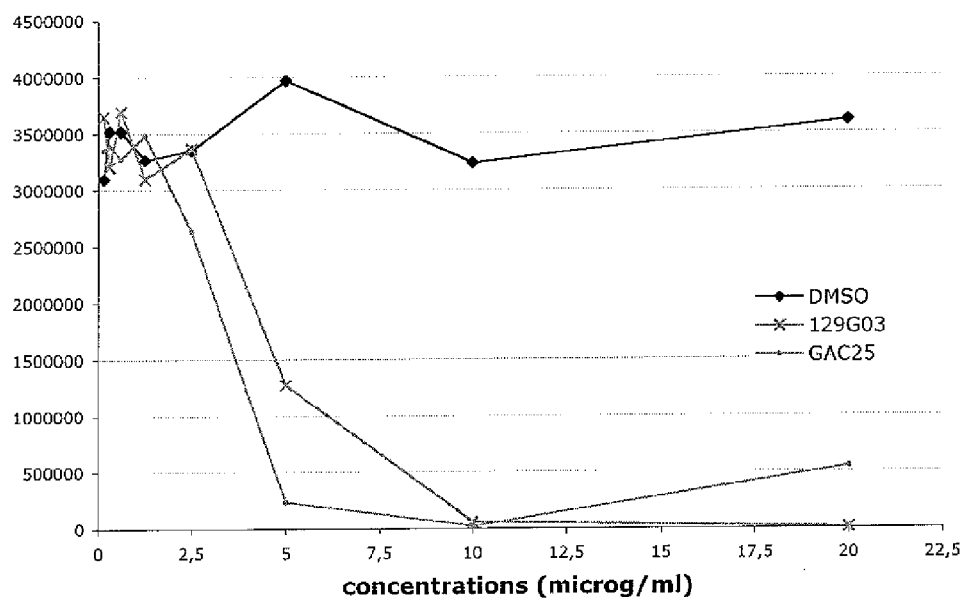
FIG. 7: Inhibition of measles virus replication in HEK-293T cells, by 129-G03 or GAC 25.

FIG. 7 shows that both 129-G03 and GAC25 blocked the in vitro replication of measles virus expressing luciferase.

Example 34

Inhibition of Measles Virus Replication in HEK-293T Cells 129-G03, GAC25 or GAC50

HEK-293T cells were infected with a recombinant measles virus expressing luciferase (MV-Luc), and treated or not with DMSO alone, 129-G03, GAC25 (A) or GAC50 (B). After 48 hours, luciferase activity was determined in total cell lysates.

Figure 8:
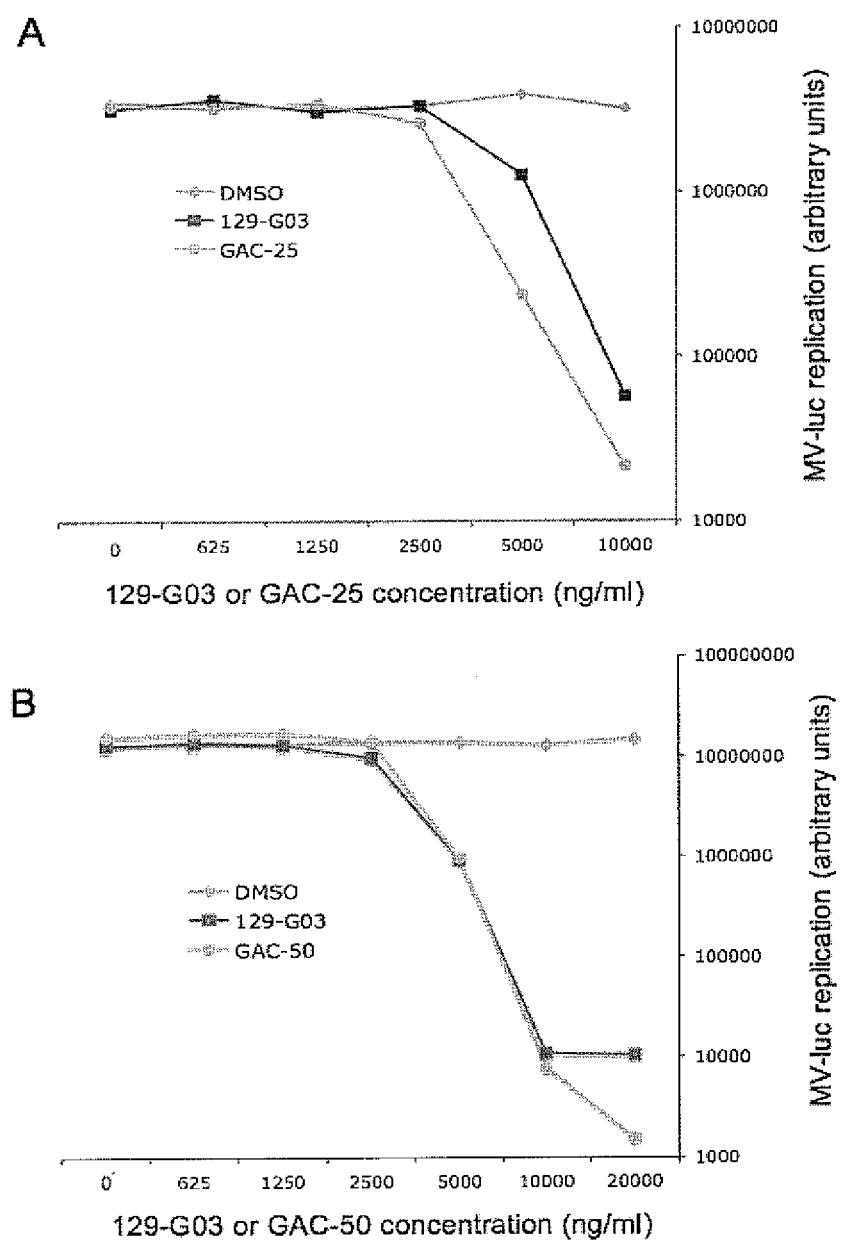
FIG. 8: Inhibition of measles virus replication in HEK-293T cells by 129-G03, GAC-25 (FIG. 8A) or GAC-50 (FIG. 8B).

The results set out in FIG. 8 demonstrate that GAC25, GAC50 and 129-G03 blocked the in vitro replication of the measles virus (MV).

Example 35

Inhibition of Chikungunya Virus (CHIKV) in HEK-293T Cells by 129-G03 or GAC50

HEK-293T cells were pre-treated with DMSO, 129-G03 or GAC50 and infected 3 hours later with CHIKV (MOI=1). Viral infection was determined 24 hours later by glycoprotein immunostaining using an anti-E2 monoclonal antibody (red fluorescence).

Figure 9:
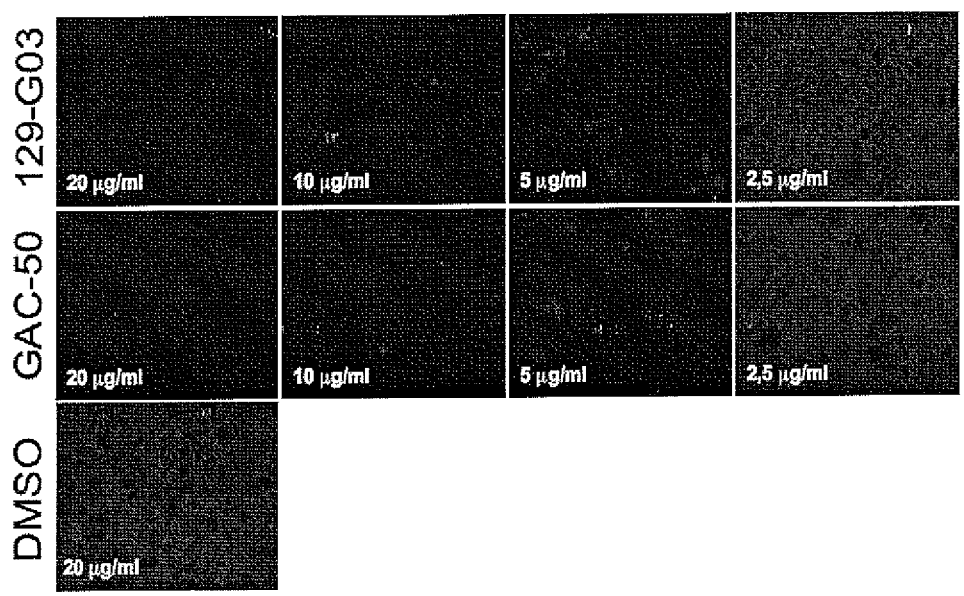
FIG. 9: Inhibition of chikungunya virus (CHIKV) in HEK-293T cells by 129-G03 or GAC-50.

The results set out in FIG. 9 demonstrate that GAC50 and 129-G03 blocked the in vitro replication of the chikungunya virus (CHIKV).

Example 36

Inhibition of Measles Virus Replication in HEK-293T Cells

Cells were infected with a recombinant measles virus expressing luciferase (MV-Luc), and treated or not with DMSO alone, 129-G03, DD771 or DD778. After 24 hours, luciferase activity was determined in total cell lysates (A). Structure of DD771 and DD778 (B).

Figure 10:
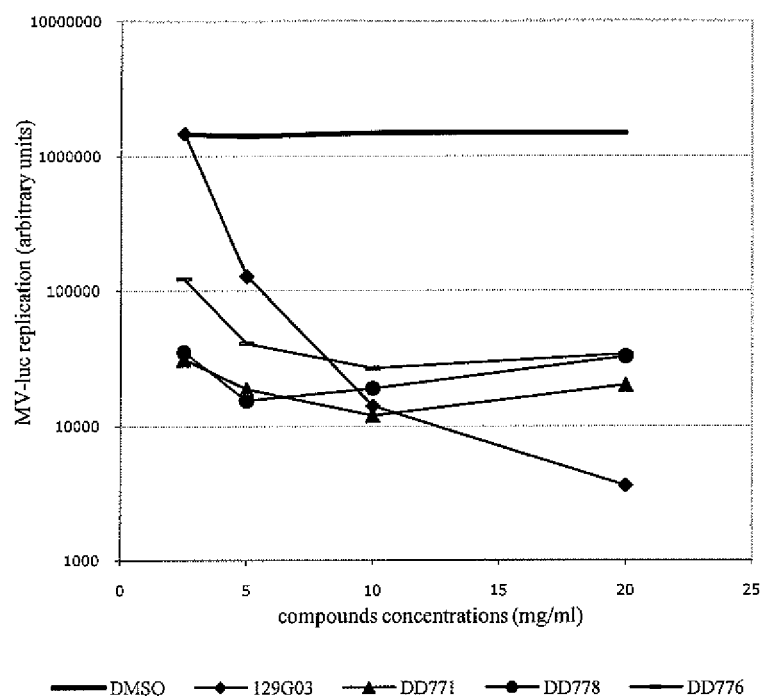
FIG. 10: Inhibition of measles virus replication in HEK-293T cells by 129-G03, DD771 or DD778.

The results set out in FIG. 10 demonstrate that DD771, DD776, DD778 and 129-G03 blocked the in vitro replication of the measles virus (MV).

Example 37

Comparison of the Effect of the 129G03 and its Analogs (GAC50 and DD771) to a Known Antiviral Compound (Ribavirin) on Virus Replication HEK-293T cells were infected with a recombinant chikungunya virus expressing renilla (Chik-ren) (A) or a recombinant measles virus expressing luciferase (MV-Luc) (B), and treated or not with DMSO alone, 129-G03, GAC50, DD771 or Ribavirin. After 24 hours, renilla or luciferase activity was determined in total cell lysates.

Figure 11:
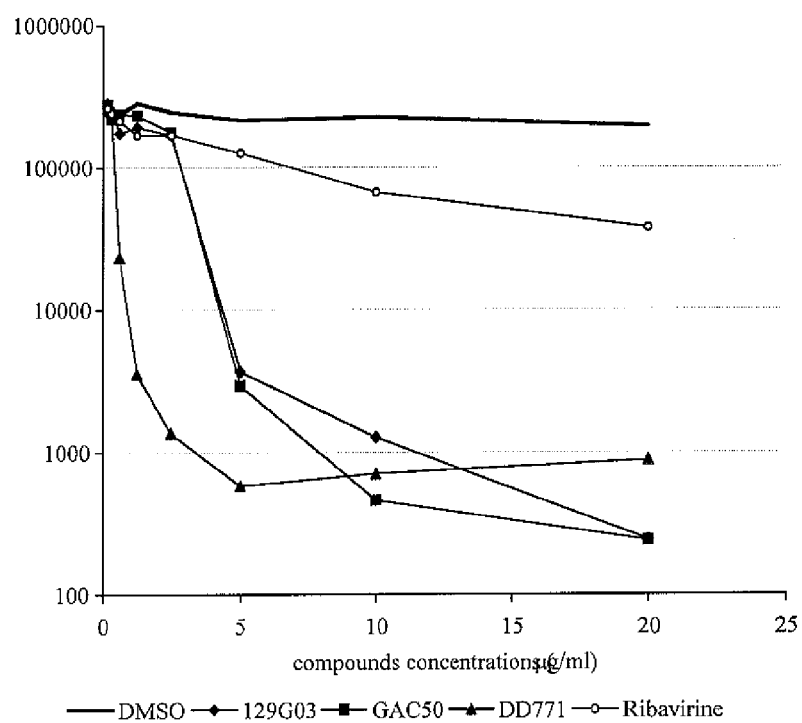
FIG. 11: Comparison of the effect of 129003, GAC 50 and DD771 to Ribavirine, a known antiviral compound on chikungunya (A) or measles (B) virus replication in HEK-293T cells.
Figure 11:
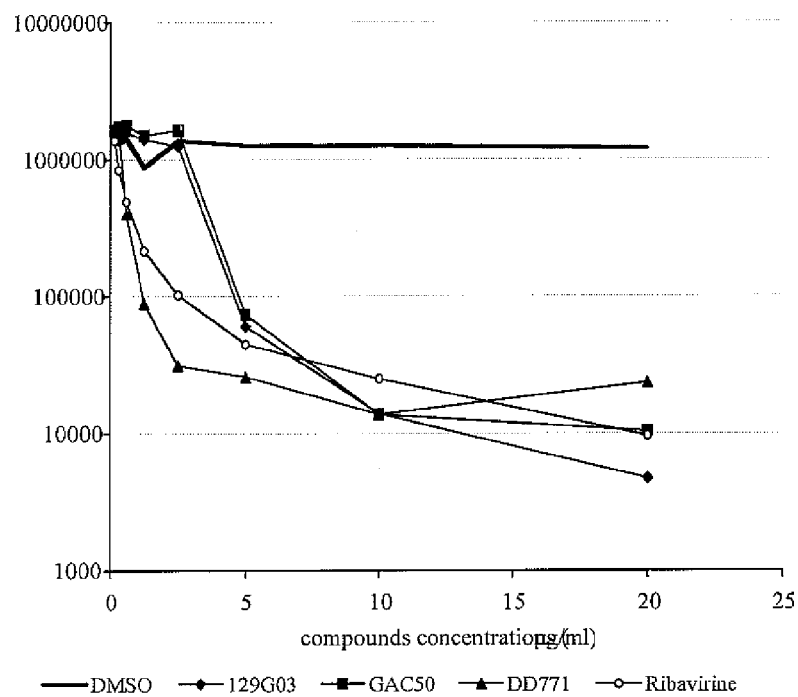

The results set out in FIG. 11 demonstrate that 129-G03, DD771, and GAC50 blocked the in vitro replication of chikungunya (CHIKV) (FIG. 11A) and measles virus (MV) (FIG. 1113).

Example 38

Inhibition of MV and CHIKV Replication by DD771

HEK-293T cells were infected with a recombinant MV strain expressing luciferase (A) or a recombinant CHIKV strain expressing renilla (B), and then treated with DMSO alone, 129-G03 or DD771 (either as a mixture or separated stereoisomers herein referred to as DD771+ and DD771−). After 24 hours, luciferase or renilla activity were determined in total cell lysates. (C) HEK-293T cells were treated with DMSO alone, 123-G05, 129-G03 or DD771 and cellular toxicity was determined by measuring intracellular ATP with the CeliTiter-Glo reagent from Promega following manufacturer's recommendation.

Figure 12:
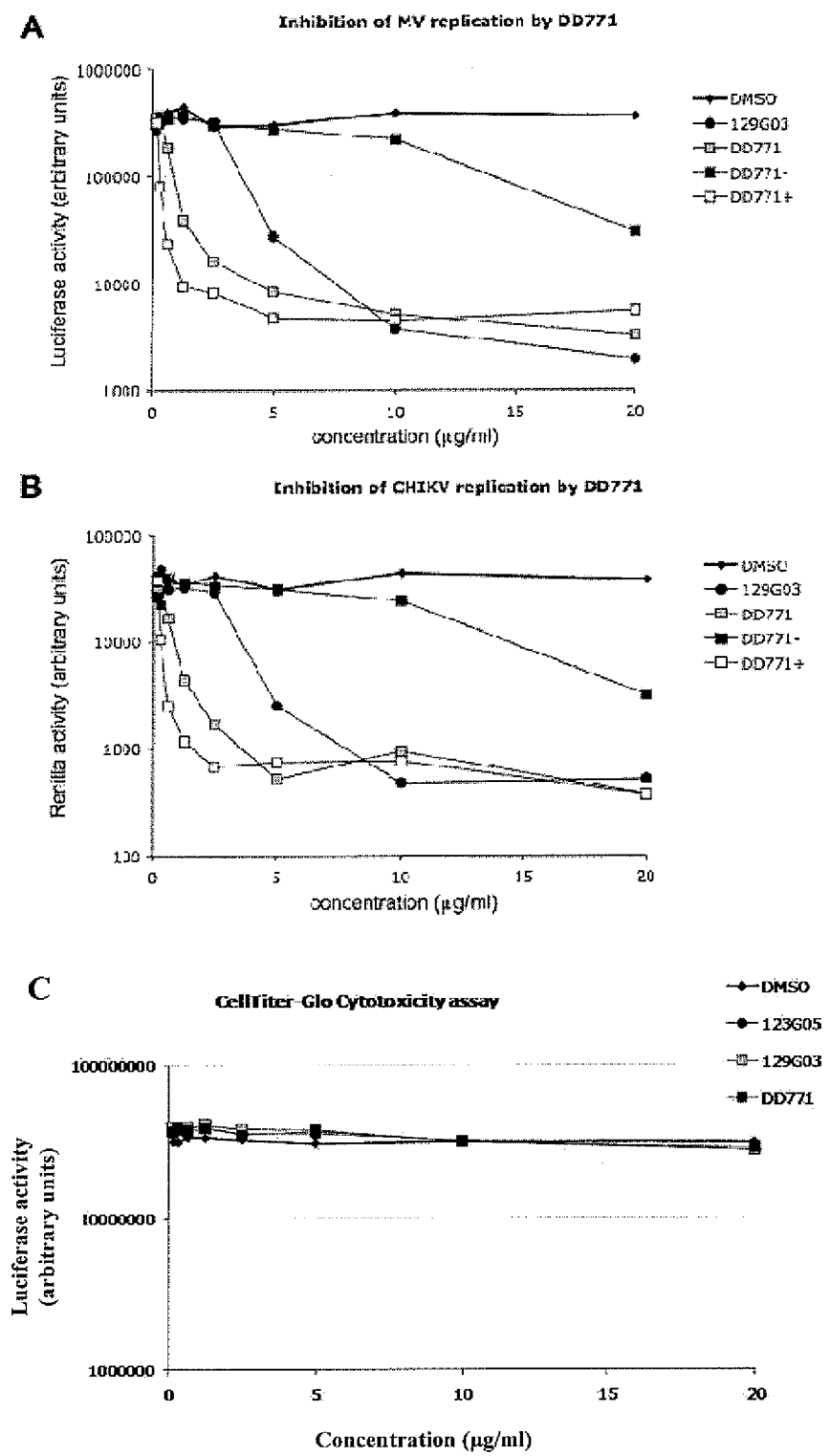
FIG. 12: Inhibition of MV (FIG. 12A) and CHIKV (FIG. 12B) replication by DD771 and cellular toxicity (FIG. 12 C) in HEK-293T cells.

As shown in FIGS. 12A and 12B, only one of the two stereoisomers was active, exhibiting an IC50 in the range of 500 nM when tested against MV or CHIKV. Further, the results set out in FIG. 12C demonstrate that 123-G05, 129-G03, and DD771 exhibit an acceptable cytotoxicity.

Example 39

Metabolic Stability

The metabolic stability of compounds DD771 and GAC50 has been measured over human liver microsomes Protocol:
Incubation (n=2)
A solution comprising each compound is prepared at a concentration of 1 mM in DMSO.

Said solution is diluted 1/100 in a phosphate buffer containing 0.5 mg/mL of human liver microsomes, 1 mM NADPH and 5 mM $MgCl_2$.

The final concentration of each compound in the assay is 2.5 μM (0.25% de DMSO).

After homogenization (30 s), 50 μL are taken and mixed to 50 μL acetonitrile in order to precipitate the proteins present in the medium and to solubilise the compound.

The mixture is vortexed during 3 min then sonicated during 3 min and finally centrifuged during 10 min at 15 000 g and 4° C.

The same treatment is done at times 15, 30, 45 and 60 minutes.

The supernatants are injected and analysed by LC-MS/MS following standard method.

In parallel, incubation is carried out and in duplicate by substituting the co-factor NADPH by an equivalent buffer volume.

A sample is taken at t=60 min only.

Analyse LC-MS/MS:

All the samples are analysed by UHPLC coupled to a triple quadruple Shimadzu LC-MS 3080.

Calculations:

Half life: $t_{1/2}=-\ln2/k$

Intrinsec clearance: $CLint=V\times\ln2/t_{1/2}$ k: disappearance rate constant ($min^{-1}$)

V=incubation volume/protein mass (μL/mg)

Results:

GAC50:

Temperature (° C.) 37

Half life (min): 11.3

Intrinsic Clearance (μL/min/mg protein): 49.1

DD771:

Temperature (° C.) 37

Half life (min): No significative metabolism

Intrinsec Clearance (μL/min/mg protein). No significative metabolism.

The invention claimed is:

1. A compound of general formula (Ia):

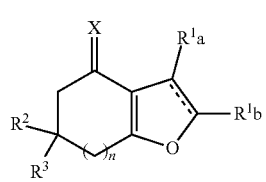

(Ia)

Wherein X is O, S, NOH, N—$NH_2$, or $NR_x$ wherein $R_x$ is H or $C_1$-$C_6$Alkyl, $R^2$, $R^3$ are H, $CH_3$, F, Cl, Br, I, NR'R", OH, C(=O)OH, $C_6$-$C_{10}$ aryl, or a 5 to 7 membered heterocycle; $R^{1b}$ is H or $NO_2$; n is 1 or 2; ---- is a double bond;

$R^{1a}$ is a ring system A:

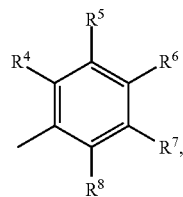

(A)

$R^4$, $R^5$, $R^6$, $R^7$ and $R^8$ are each independently selected from H, Cl, Br, I, F, OH, $C_1$-$C_6$ alkyl, $C_2$-$C_8$ alkenyl, $C_1$-$C_6$ fluoroalkyl, $C_1$-$C_6$ fluoroalkoxy, $NO_2$, and $C_1$-$C_6$ alkoxy, or two of $R_4$, $R_5$, $R_6$, $R_7$, $R_8$ together form with the carbon atoms to which they are attached a 1,3-dioxolane or a 1,4-dioxane;

when R2 and R3 are CH3, then $R_{1b}$ cannot be $NO_2$; and with the exclusion of the compounds of formula (Ia) wherein: X is O; $R^{1b}$ is H or $NO_2$; $R_2$=$R_3$ are H or $CH_3$; $R^{1a}$ is m- or p-$NO_2$Ph; n is 1;

and the stereoisomeric forms, mixtures of stereoisomeric forms or pharmaceutically acceptable salts forms thereof.

2. The compound of claim 1, which is selected from:
3-(5-chloro-2-methoxyphenyl)-6,7-dihydro-5H-benzofuran-4-one;
3-(3-bromophenyl)-6,7-dihydro-5H-benzofuran-4-one;
3-(3-fluorophenyl)-6,7-dihydro-5H-benzofuran-4-one;
3-(4-chlorophenyl)-6,7-dihydro-5H-benzofuran-4-one;
3-(2-chlorophenyl)-6,7-dihydro-5H-benzofuran-4-one;
3-(3-methoxyphenyl)-6,7-dihydrobenzofuran-4(5H)-one;
3-(3,5-dichlorophenyl)-6,7-dihydro-5H-benzofuran-4-one;
3-((3-trifluoromethyl)phenyl)-6,7-dihydro-5H-benzofuran-4-one;
3-(3-benzyloxyphenyl)-6,7-dihydro-5H-benzofuran-4-one;
3-(3,4,5-trimethoxyphenyl)-6,7-dihydro-5H-benzofuran-4-one;
3-(3,4-dichlorophenyl)-6,7-dihydro-5H-benzofuran-4-one;
3-(3-iodo-4-methoxyphenyl)-6,7-dihydro-5H-benzofuran-4-one;
3-(3-iodophenyl)-6,7-dihydro-5H-benzofuran-4-one;
3-(3-chlorophenyl)-6,7-dihydro-5H-benzofuran-4-one;
3-(3-chlorophenyl)-6,6-dimethyl-6,7-dihydro-5H-benzofuran-4-one;
3-(3-chlorophenyl)-6-methyl-6,7-dihydro-5H-benzofuran-4-one;
1-[4-(3-chlorophenyl)-2-methyl-5-nitro-4,5-dihydrofuran-3-yl]ethanone;
3-(3-Chlorophenyl)-6,7-dihydro-5H-benzofuran-4-one oxime;
3-(3-iodophenyl)-6,7-dihydro-5H-benzofuran-4-one (GAC 25);
3-(3-ethenylphenyl)-6,7-dihydro-5H-benzofuran-4-one (GAC 50);
3-(3-methylphenyl)-6,7-dihydro-5H-benzofuran-4-one (GAC 22); and
3-(2,3-dichlorophenyl)-6,7-dihydro-5H-benzofuran-4-one (GAC 20).

* * * * *